United States Patent
Hall

(10) Patent No.: US 9,464,150 B2
(45) Date of Patent: Oct. 11, 2016

(54) MOLECULARLY IMPRINTED POLYMERS

(71) Applicant: The University of Kent, Chatham, Kent (GB)

(72) Inventor: Andrew Hall, Chatham (GB)

(73) Assignee: The University of Kent, Chatham, Kent (GB)

( * ) Notice: Subject to any disclaimer, the term of this patent is extended or adjusted under 35 U.S.C. 154(b) by 0 days.

(21) Appl. No.: 14/423,208

(22) PCT Filed: Aug. 22, 2013

(86) PCT No.: PCT/GB2013/052214
§ 371 (c)(1),
(2) Date: Feb. 23, 2015

(87) PCT Pub. No.: WO2014/030002
PCT Pub. Date: Feb. 27, 2014

(65) Prior Publication Data
US 2015/0225499 A1    Aug. 13, 2015

(30) Foreign Application Priority Data
Aug. 24, 2012 (GB) .................................. 1215175.9

(51) Int. Cl.
| | | |
|---|---|---|
| C08F 222/14 | (2006.01) | |
| C07D 213/75 | (2006.01) | |
| C08F 226/06 | (2006.01) | |
| G01N 33/82 | (2006.01) | |

(52) U.S. Cl.
CPC ........... *C08F 222/14* (2013.01); *C07D 213/75* (2013.01); *C08F 226/06* (2013.01); *G01N 33/82* (2013.01)

(58) Field of Classification Search
CPC ........................... C08F 222/14; C07D 213/75
See application file for complete search history.

(56) References Cited

PUBLICATIONS

Piletska et al, "Biotin-Specific Synthetic Receptor Using Molecular Imprinting" Anal. Chim. Acta., vol. 54, No. 1, pp. 179-183 (2004).*
Takeuchi et al., "Molecular Imprinting of Biotin Derivative and Its Application to Competitive Binding Assay Using Noniosotopic Labeled Ligand," Anal. Chem., vol. 72, No. 11, pp. 2418-2422 (2000).*
Wiklander et al., "Towards a Synthetic Avidin Mimic," Anal. Bioanl. Chem., vol. 4000, No. 5, pp. 1392-1404 (2011).*
Andersson, L.I. et al., "Mimics of the Binding Sites of Opioid Receptors Obtained by Molecular Imprinting of Enkephalin and Morphine," Proc. Natl. Acad. Sci., vol. 92, pp. 4788-4792 (1995).
Özcan, A.A. et al., "Semi-Synthetic Biotin Imprinting onto Avidin Crosslinked Gold-Silver Nanoparticles," J. Nanopart. Res., vol. 14, No. 945, pp. 1-8 (2012).
Sellergren, B. et al., "Highly Enantioselective and Substrate-Selective Polymers Obtained by Molecular Imprinting Utilizing Noncovalent Interactions. NMR and Chromatographic Studies on the Nature of Recognition," J. Am. Chem. Soc., vol. 110, pp. 5853-5860 (1988).
Sellergren, B., "Polymer- and Template-Related Factors Influencing the Efficiency in Molecularly Imprinted Solid-Phase Extractions," Trends Anal. Chem., vol. 18, No. 3, pp. 164-174 (1999).
Shea, K.J. et al., "Polymer Complements to Nucleotide Bases. Selective Binding of Adenine Derivatives to Imprinted Polymers," J. Am. Chem. Soc., vol. 115, No. 8, pp. 3368-3369 (1993).
Suriyanarayanan, S. et al., "Biotinyl Moiety-Selective Polymer Films with Highly Ordered Macropores," Chem. Commun., vol. 49, pp. 5274-5276 (2013).
International Search Report for PCT/GB2013/052214, published as WO 2014/030002 A3 on Feb. 27, 2014 (3 pages).
Piletska, E. et al., "Biotin-Specific Synthetic Receptors Prepared Using Molecular Imprinting," Anal. Chim. Acta, vol. 54, No. 1, pp. 179-183 (2004).
Takeuchi, T. et al., "Molecular Imprinting of Biotin Derivatives and Its Application to Competitive Binding Assay Using Nonisotopic Labeled Ligands," Anal. Chem., vol. 72, No. 11, pp. 2418-2422 (2000).
Wiklander, J. et al., "Towards a Synthetic Avidin Mimic," Anal. Bioanal. Chem., vol. 400, No, 5, pp. 1397-1404 (2011).

* cited by examiner

*Primary Examiner* — Robert Harlan
(74) *Attorney, Agent, or Firm* — Bookoff McAndrews, PLLC

(57) ABSTRACT

The present invention refers to new classes of polymerizable monomers targeting biotin, a biotin derivative, a biotin analog or a biotinylated molecule and related structures, as well as molecularly imprinted polymers obtainable by polymerization of at least one of these monomers and at least one cross-linking monomer in the presence of a suitable template molecule. The obtained polymers may be used for separation of biotin and related small molecules, together with larger biotinylated molecules of biological origin, e.g. proteins, from complex mixtures. The monomer comprises i) an isophthalic acid derivative or a pyridine-2,6-dicarboxylic acid derivative and ii) a vinyl-2-aminopyridine derivative.

29 Claims, 1 Drawing Sheet

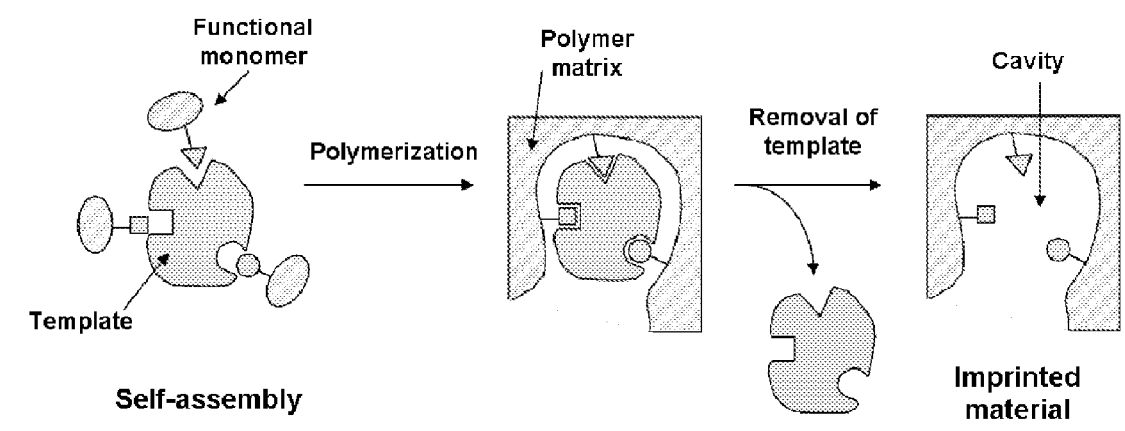

MOLECULARLY IMPRINTED POLYMERS

This application is a national stage filing under 35 U.S.C. §371 of International Application No. PCT/GB2013/052214, filed on Aug. 22, 2013, which claims the benefit of priority to United Kingdom Patent Application No. GB 1215175.9, filed on Aug. 24, 2012.

The present invention relates to a polymerisable monomer and its use, after polymerisation, as a molecularly imprinted polymer for the capture of biotin, a biotin derivative, a biotin analogue or a biotinylated molecule.

In medical, food, environmental and chemical sciences, there is an increasing need for the selective separation of specific substances from complex mixtures of related substances. The end goal may be the preparative isolation of a certain compound or compounds, their analytical quantitation or the removal of impurities and/or unwanted side reagents from a reaction.

Current methods for selection, recognition and capture of compounds include the use of enzymes, antibodies, DNA and other biologically active compounds. While the use of biological capture molecules is preferred due to their high selectivity and affinity for their target, the use of such molecules is usually lengthy, expensive and often difficult to reproduce and repeat on a large scale. The use of synthetic alternatives has been investigated, an example of which is Molecularly Imprinted Polymers.

A Molecularly Imprinted Polymer (MIP) is a polymer that has been prepared using molecular imprinting which leaves cavities in a polymer matrix with affinity to a chosen "template" molecule. The process usually involves initiating the polymerisation of monomers in the presence of a template molecule that is extracted afterwards, thus leaving complementary cavities behind.

MIPs usually exhibit a high selectivity towards their substrate, analogous to antibody-antigen recognition (R. A. Bartsch, M. Maeda, Eds., Molecular and Ionic Recognition with Imprinted Polymers (Oxford University Press, Washington, 1998)) and sufficient affinity for the original, template molecule. A fast and cost-effective molecularly imprinted polymer technique has applications in many fields of chemistry, biology and engineering. Applications of MIPs are known, for example as affinity material for sensors, detection of chemical, antimicrobial and dye residues in food, adsorbents for solid phase extraction, binding assays, artificial antibodies, chromatographic stationary phase, catalysis, chemical separations, drug development and screening, and by-product removal in chemical reaction. The technique has shown promise in chiral separations of, for example, amino acid derivatives, peptides, phosphonates, aminoalcohols and beta-blocking compounds, affinity chromatography of nucleotides and the DNA-bases, as well as substitutes for antibodies in immunoassays for commercial drugs (Andersson et al (1995) *Proc. Natl. Acad. Sci.* 92: 4788-92). Generally, MIPs offer a number of advantages compared to natural receptors and antibodies. These include high mechanical, thermal and chemical stability, excellent operational and storage stability, simplicity of manufacturing and comparatively low price for material preparation.

Molecular imprinting is akin to making an artificial lock for a specific molecule that serves as a key. One of the greatest advantages of artificial receptors over naturally occurring ones is freedom of molecular design. The frameworks of artificial receptors are never restricted to proteins and a variety of skeletons (e.g., carbon chains and fused aromatic rings) can be used. Thus, the stability, flexibility, and other properties are freely modulated according to need. Even functional groups that are not found in nature can be employed in these man-made compounds. Furthermore, when necessary, the activity to response towards outer stimuli (photo-irradiation, pH change, electric or magnetic field, and others) can be provided by using appropriate functional groups. The spectrum of functions is far wider than that of naturally occurring receptors and capture molecules.

Molecular imprinting (MI) generally comprises the key steps shown in FIG. 1. Monomers, termed functional monomers, are allowed to interact reversibly with a template molecule in solution. The template-monomer assemblies are copolymerized with a cross-linking monomer, resulting in a three-dimensional network polymer. The template is then displaced leaving an imprinted polymer that can be used for selective molecular recognition of the template compound or related substances.

MIPs of the correct size/shape may be packed in chromatographic columns and used for chromatographic separation of the template and related compounds from complex mixtures, on both analytical and preparative scales. Preparative applications can be separation of a compound from a complex mixture and isolation of the compound, e.g. through an affinity chromatography procedure where the strength of interactions with the stationary phase may be controlled through mobile phase modification. Further potential analytical applications are in competitive binding assays, chemical sensors or selective sample enrichments (Sellergren (1999) *Trends Anal. Chem.* 18: 164-174).

Non-covalent imprinting remains the most widely applied technique to generate molecularly imprinted binding sites (Sellergren et al (1988) *J. Am. Chem. Soc.* 110: 5853-60). This makes use of non-covalent self-assembly of the template with functional monomers prior to polymerisation, free radical polymerisation with a cross-linking monomer and then template extraction followed by rebinding by non-covalent interactions. This method is technically simple but relies on the success of stabilisation of the relatively weak interactions between the template and the functional monomers. Stable monomer-template assemblies will, in turn, lead to higher concentrations of high affinity binding sites in the resulting polymer.

Materials for MIPs may be synthesised in any standard equipped laboratory in a relatively short time and some MIPs exhibit binding affinities and selectivities in an order of those exhibited by antibodies towards their antigens. Most MIPs are synthesised by free radical polymerisation of functional monounsaturated (vinylic, acrylic, methacrylic) monomers and an excess of cross-linking di- or tri-unsaturated (vinylic, acrylic, methacrylic) monomers resulting in porous organic network materials. These polymerisations are relatively robust, allowing polymers to be prepared in high yield using different solvents (aqueous or organic) and at different temperatures. This is necessary in view of the varying solubilities of the template molecules.

The most successful non-covalent imprinting systems are based on commodity acrylic or methacrylic monomers, such as methacrylic acid (MAA), cross-linked with ethyleneglycol dimethacrylate (EDMA). Initially, derivatives of amino acid enantiomers were used as templates for the preparation of imprinted stationary phases for chiral separations (MICSPs), but this system has proven generally applicable to the imprinting of templates capable of engaging in hydrogen bonding or electrostatic interactions with MAA (Shea et al (1993) *J. Am. Chem. Soc.* 115: 3368-3369).

There are some classes of compound for which the generation of MIPs remains problematic, thus demanding the development of new functional monomers which are able to bind, preferably strongly, with such templates. One such example is biotin (vitamin H/B$_7$), which is necessary for cell growth, the production of fatty acids and the metabolism of fats and amino acids. Biotin is known to bind to the proteins streptavidin and avidin with one of the highest affinities known, with $K_d$ ca. $10^{-14}$ to $10^{-15}$ M. The strength of this interaction is used extensively in biochemical assays. Here, biotin is conjugated to proteins, or other biomacromolecules. Because biotin is a small molecule (MW=244.31), the biological activity of the biological molecule or biomacromolecule is generally unaffected. Any biotinylated biomacromolecule within the sample may then be extracted through incubation with (strept)avidin-modified stationary phases, while non-biotinylated molecules are simply washed away. The biotinylated molecules of interest may then be released through a thermal or chemical treatment of the stationary phase.

Although the avidin-biotin system is recognised as a useful tool for highly sensitive detection, it works only in aqueous solution. Therefore, the development of stable avidin-like materials with binding properties for biotin derivatives in organic solvents may enable the development of new avidin-biotin applications.

As with most biological-based systems, there are problems with the stability and storage of (strept)avidin-modified stationary phases and also limitations with the conditions under which they may be used. By contrast, MIPs are exceptionally robust materials, able to withstand extremes of pH and elevated temperature (to ca. 140° C.) and to be used in both aqueous and organic solvent environments. MIPs are also substantially cheaper to prepare than their biological counterparts. The ability to prepare a synthetic avidin via molecular imprinting will therefore lead a wide range of applications.

Previous attempts to create a MIP for the recognition of biotin have been reported, but have relied upon the use of excesses of commercially-available functional monomers, cocktails thereof chosen after computer modelling or from the use of a 2-amidopyridine monomer under poorly chosen conditions. For example, Wiklander et al (*Analytical and Bioanalytical Chemistry* (2011) 400(5): 1397-1404) prepared a MIP using a 4× excess of MAA as functional monomer, with respective to the template (biotin methyl ester), and found that polymerisation gave a polymer with a heterogeneous distribution of binding sites. The MIP showed a low population (7.7 µmol/g polymer) of high affinity sites with $K_d=4\times10^{-6}$ M and a far higher population (65 µmol/g polymer) of lower affinity sites ($K_d=1.6\times10^{-4}$ M). The binding here, measured in the non-competitive organic solvent chloroform, is at least eight orders of magnitude lower than for binding of biotin to streptavidin in water, while the heterogeneity of binding sites poses a further problem. For example, in solid phase extraction, it is ideal if the solid phase extracts the target under one set of conditions (only) and releases all of the captured target under another set of conditions. Heterogeneous binding site distributions can mean that one or neither of these conditions is met. Also, the risk of non-specific binding to non-target species is increased if the binding site distribution is heterogeneous.

Takeuchi et al (*Anal. Chem.* (2000) 72: 2418-2422) compared the use of MAA as a functional monomer against 2-(trifluoromethyl)acrylic acid (TFAA), with EDMA as a cross-linker. The results show that MAA forms a MIP that binds biotin more effectively than a MIP generated from TFAA. While TFAA would be expected to be a more effective MIP because it is a stronger acid, the authors speculate that the lower binding affinity of the TFAA MIP is because TFAA is a good hydrogen bond donor but a weaker hydrogen bond acceptor. In contrast, MAA is a weaker acid and so acts as both a hydrogen bond donor and acceptor.

Piletska et al (*Anal Chim Acta* (2004) 504: 179-183) also investigated the use of MAA in a MIP for the capture of biotin. MAA as a monomer was compared with TFAA and 2-acrylamindo-2-methylpropanesulphonic acid (AMPSA), using N,N'-methylenebisacrylamide (MBAA) as a cross-linker. The resulting MIPS were photografted onto the surface of polystyrene microspheres with the aim of developing MIPs that are suitable for use in aqueous conditions. The best results were seen, again, with MAA but the results also showed that the MIPs functioned more effectively when supported on the microspheres suggesting that the MIP is highly flexible under aqueous conditions.

A recent paper by Ozcan et al (*J. Nanoparticle Res.* (2012) 14(6): 1-8) took a different approach to the design of a MIP for biotin. The resulting MIP was a semi-synthetic biotin-imprinted polymeric shell that is decorated on its surface with avidin cross-linked Au/Ag nanoclusters. The MIP showed a $K_a$ of $3.89\times10^6 M^{-1}$ ($K_d=2.57\times10^{-6}$ M or 2.57 µM) and was highly re-usable. The methodology described in the paper is a different type of imprinting, i.e. in inorganic polymers (silica) rather than the organic polymers that are more robust, both in preparation and usage. While silica-based materials are more heat stable, they tend to be less pH stable.

Recently, a hierarchical molecular imprinting strategy has been described (Suriyanarayanan et al., (2013) *Chem. Commun.*, 49: 5274-5276) wherein macroporous films with recognition sites selective for biotinylated compounds are prepared and their binding characteristics assessed via quartz crystal microbalance (QCM) measurements. These materials were prepared via the electro-polymerisation of commodity monomers—p-aminobenzoic acid and pyrrole—in the presence of biotin as template. The binding of only one biotin derivative (biotin methyl ester) is reported while the binding capacity of the imprinted films is not assessed.

Thus, there remains a need for a non-biological capture agent for biotin, biotin derivatives, biotin analogues and/or biotinylated molecules. The present invention seeks to overcome the problems of existing biotin-capturing MIPs by providing a novel functional monomer that recognises biotin, biotin derivatives, biotin analogues and/or biotinylated molecules. The monomer is suitable for polymerisation and the molecular imprinting of biotin, biotin derivatives, biotin analogues and/or biotinylated molecules to create an imprinted material that is selective for biotin, biotin derivatives, biotin analogues, relates substances and biotinylated biomacromolecules.

In particular, the invention encompasses a polymerisable monomer containing a recognition cleft for biotin, a biotin derivative, a biotin analogue or a biotinylated molecule comprising an isophthalic acid derivative or a pyridine-2,6-dicarboxylic acid derivative and a vinyl-2-aminopyridine derivative for use as part of a molecularly imprinted polymer.

Expressed in another way, the invention resides in a polymerisable monomer prepared from i) an isophthalic acid derivative or a pyridine-2,6-dicarboxylic acid derivative, ii) a vinyl-2-aminopyridine derivative and optionally iii) a 2-aminopyridine derivative, to define a recognition cleft for biotin, a biotin derivative, a biotin analogue or a biotinylated molecule.

Previous attempts to create a biotin-selective MIP have used a monomer created from a single building block. In contrast, the functional monomer of the present invention is created from two different building blocks. In this way, the resulting monomer is shaped to contain a dipodal cleft formed by a diacid unit and two 2-aminopyridine units, at least one of which contains a vinyl group. As a result, the cleft is decorated with complementary hydrogen-bond sites that are spatially arranged within the cleft in a manner that allows for biotin binding. The monomer itself is not specific for biotin, biotin derivatives, biotin analogues or biotinylated molecules. Rather, the biotin specificity arises from the imprinting of the template-monomer complex. The use of the two building blocks also imparts structural rigidity to the monomer, thereby overcoming some of the drawbacks associated with the previously known monomers.

The monomers also possess at least one polymerisable function through at least one vinyl group. The monomer is used stoichiometrically with respect to the template (biotin, biotin derivative, biotin analogue or biotinylated molecule) species, i.e. in a 1:1 ratio, and so when polymerised, the resulting polymer provides a large population of uniform binding sites with high affinity for biotin, derivatives and analogues thereof and/or biotinylated molecules.

In one embodiment, the ratio of the isophthalic acid derivative to the vinyl-2-aminopyridine derivative is 1:2. Alternatively, the ratio of the isophthalic acid derivative to the vinyl-2-aminopyridine derivative is 1:1 and the monomer further includes a 2-aminopyridine unit.

Preferably the monomer is the compound of Formula (I):

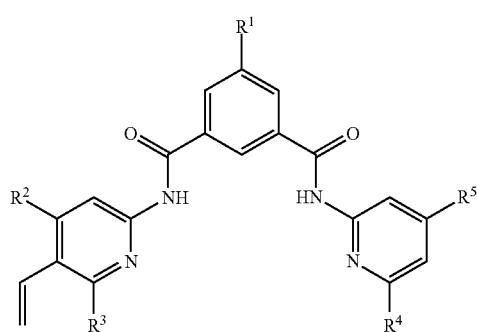

(I)

In an alternative embodiment, the monomer may be the compound of Formula (II):

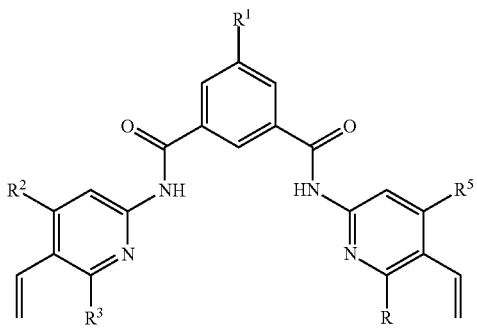

(II)

As will be seen from the structure of biotin below (Formula III), the cleft offered by the monomer provides a snug fit for biotin, a biotin derivative, a biotin analogue or a biotinylated molecule, which forms hydrogen bonds between the amido groups and the pyridine rings of the 2-aminopyridine derivatives on either side of the cleft.

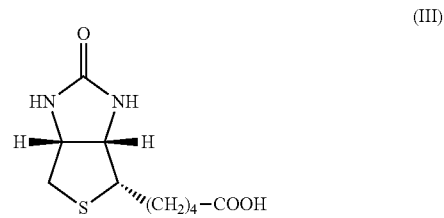

(III)

The isophthalic acid derivative provides an exact width, or bridge, to the cleft, to space the 2-aminopyridine derivatives. The structure also provides the required rigidity to the monomer.

In both formulas, $R^1$, $R^2$, $R^3$, $R^4$ and $R^5$ may be independently selected from the group consisting of H, alkyl with 1-10 carbon atoms, alkoxy with 1-10 carbon atoms, aryl with up to five substituents, amino, amido and halogen.

The $R^1$ group is preferably chosen to impart a desired solubility to the monomer. For example, $R^1$ may be a methyl, ethyl, propyl, tert-butyl, methoxy, ethoxy, propxy, butoxy or benzyloxy group. A monomer wherein $R^1$ is tert-butyl has been found to be particularly suitable because of the ready commercial availability of 4-tert-butylisophthalic acid.

Groups $R^2$ to $R^5$ are selected both to assist in increasing monomer solubility and also to affect the basicity of the pyridine ring nitrogen. Groups $R^2$-$R^5$ are preferentially hydrogen or methyl groups, due to the ready commercial availability of starting materials for preparation of these vinyl-2-aminopyridine building blocks.

In a further embodiment, the acid derivative is a substituted 2,6-pyridine dicarboxylic acid derivative. The pyridine group leads to increased rigidity of the cleft through hydrogen bonding, thereby increasing the biotin binding affinity of the monomers.

Expressed in another way, the monomer of the invention is the compound of formula (IV):

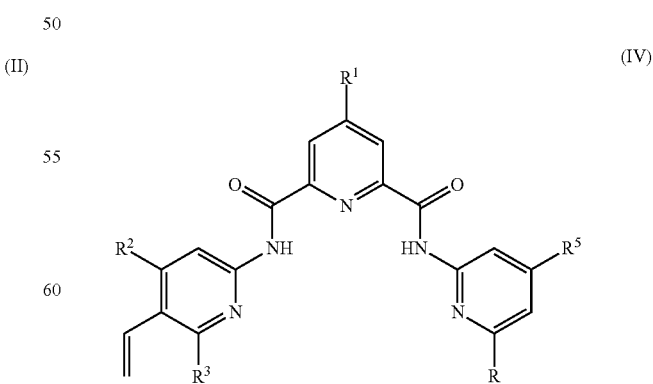

(IV)

Alternatively, the monomer of the invention is the compound of formula (V):

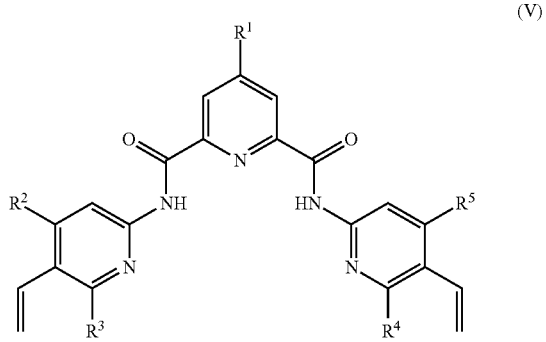
(V)

In formulas IV and V, $R^1$, $R^2$, $R^3$, $R^4$ and $R^5$ may be independently selected from the group comprising: H, alkyl with 1-10 carbon atoms, alkoxy with 1-10 carbon atoms, aryl with up to five substituents, amino, amido and halogen.

$R^1$ may be any alkyl group, such as methoxy, ethoxy, etc., but preferably, $R^1$ is 3-methylbutoxy. Also preferable is a compound of Formula IV or Formula V wherein $R^2$, $R^3$, $R^4$ and $R^5$ are either H or methyl. The same considerations apply to Formulas IV and V as they do to Formulas I and II when selecting groups suitable for the desired hydrogen bonding and strength of the monomer.

Most preferably, the diacid derivative is 5-t-butyl-isophthaloyl dichloride or 4-(3-methylbutoxy)-2,6-pyridinedicarboxylic acid dichloride. Ideally, the vinyl-2-aminopyridine derivative is 2-amino-5-vinylpyridine.

The monomer of the invention may be made by any suitable method. For example, the method comprises reacting two equivalents of a vinyl-2-aminopyridine derivative with one equivalent of an isophthalic acid derivative or a pyridine-2,6-dicarboxylic acid derivative in the presence of a tertiary amine, such as triethylamine. Any tertiary amine will be suitable for use in the method, as well as the use of standard procedures well known to the skilled person.

In particular the method comprises:
a) dissolving a diacid derivative in a solution using an appropriate anhydrous solvent, e.g. dichloromethane, chloroform or tetrahydrofuran;
b) cooling the mixture to 0° C.;
c) adding a solution of vinyl-2-aminopyridine derivative and a tertiary amine;
d) warming the mixture to room temperature and stirring for 24 hours; and
e) quenching the reaction by addition of water, separating the resulting organic and aqueous phases, washing and drying the organic phase, then evaporating the solvent to give the solid monomer.

In one embodiment, the ratio of the diacid derivative to the vinyl-2-aminopyridine derivative is 1:2. In another embodiment, the ratio of the diacid derivative to the vinyl-2-aminopyridine derivative is 1:1 and the method further comprises adding one equivalent of 2-aminopyridine before addition of one equivalent of a vinyl-2-aminopyridine derivative.

Isophthalic acid derivatives, vinyl-2-aminopyridine derivatives and 2-aminopyridine are commercially available or can be made by standard methods well known to the skilled person or methods analogous thereto, see for example Advanced Organic Chemistry by Jerry March, 4th Edition, John Wiley & Sons, 1992, Organic Syntheses, Volumes 1-8, John Wiley, edited by Jeremiah P. Freeman (ISBN: 0-471-31192-8), 1995, Fiesers' Reagents for Organic Synthesis, Volumes 1-17, John Wiley, edited by Mary Fieser (ISBN: 0-471-58283-2), and Handbook of Heterocyclic Chemistry, A. R. Katritzky et al, 3rd Edition, Elsevier, 2010.

The invention also encompasses a MIP obtained by polymerisation of at least one of the monomers described above with at least one cross-linking monomer in the presence of a template molecule, wherein the template molecule is selected from the group consisting of biotin, a biotin derivative and a biotinylated molecule.

The biotin derivative may be any salt including ester, amide, carbonate and carbamate.

The cross-linker may be any suitable di-, tri- or tetra-vinyl monomer and will usually be selected according to the environment in which the polymer is to be used. For example, a polymer for use in organic media will require the use of a cross-linking monomer that has some hydrophobicity. Suitable cross-linking monomers in this instance include ethyleneglycol dimethacrylate, divinyl benzene and trimethyloylpropane trimethacrylate. In contrast, a polymer that is to be used in an aqueous environment will require the use of a more hydrophilic cross-linking monomer. Suitable cross-linking monomers include bisacrylamides and pentaerythritol triacrylate.

The invention also relates to free-radical polymerisation of at least two of the monomers described above with at least one cross-linking monomer, in the presence of a template molecule, wherein the template molecule is selected from the group consisting of biotin, a biotin derivative and a biotinylated molecule.

Specifically the method comprises the steps of:
i) formation of a template-functional monomer complex in a suitable solvent using non-covalent binding;
ii) polymerisation with an excess of a cross-linking reagent initiated by a suitable polymerisation initiator; and
iii) removal of the template to yield a complementary binding site for the template, wherein the template is selected from the group consisting of biotin, a biotin derivative and a biotinylated molecule and the functional monomer is selected from the functional monomers described above.

The template may be biotin or a derivative thereof, such as an ester, amide, carbonate or carbamate.

Typical solvents used in the method include toluene, chloroform, acetonitrile, tetrahydrofuran and dimethylformamide. Such solvents can also act as porogens, creating pores in the material which aid transport processes.

Any suitable polymerisation initiator may be used, for example azobisisobutyronitriles such as 2,2'-azobis(2,4-demethyl valeronitrile) and 2,2'-azobis(4-methoxy-2,4-deimethyl valeronitrile).

After polymerisation, the template may be removed from the polymer by a washing procedure, such as a continuous extraction with methanol, dilute aqueous acid or another suitable solvent system capable of breaking the non-covalent bonds between the template and the polymeric binding site.

Still further, the invention relates to the use of a polymer as described above for the separation of the template molecule, related molecules and biotinylated macromolecules from complex mixtures. Immobilisation using the MIP of the present invention may be used to develop many applications with the addition of functionalities to the biotin-binding polymers, such as chiral stationary phase, sensing materials and specific adsorbents.

The invention will now be described in more detail by way of the following non-limiting examples.

EXAMPLE 1

The monomer of Formula I, where $R^1$, $R^2$, $R^3$, $R^4$ and $R^5$ are all hydrogen, is synthesised in two steps by the reaction shown below:

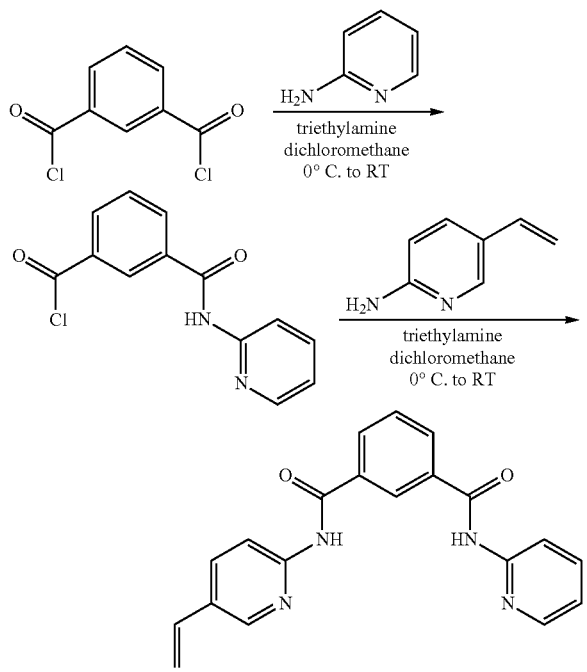

Isophthaloyl dichloride (102 mg, 0.5 mmol) is dissolved in anhydrous dichloromethane (20 mL) and placed under a dinitrogen atmosphere. The solution is then cooled to 0° C. using an ice bath. A solution of 2-aminopyridine (94 mg, 0.5 mmol) and triethylamine (51 mg, 0.5 mmol) in 10 mL dichloromethane is added dropwise to the cooled acid chloride solution. On completion of the addition, the ice bath is removed and the solution is allowed to stir at room temperature for 3 hours. At this point, the solution is cooled again to 0° C. using an ice bath and a solution of 2-amino-5-vinylpyridine (60 mg, 0.5 mmol) and triethylamine (51 mg, 0.5 mmol) in 10 mL dichloromethane is added dropwise to the cooled solution. On completion of the addition, the ice bath is removed and the solution allowed to stir at room temperature overnight. The reaction is then quenched by the addition of 10 mL water. The organic and aqueous layers are separated, then the organic layer is washed with saturated aqueous sodium hydrogen carbonate solution (2×10 mL) and water (10 mL), before being dried over magnesium sulfate. After filtration, the solvent is evaporated under reduced pressure. The residue is then purified by column chromatography using silica gel as the stationary phase and ethyl acetate/hexanes as the mobile phase, to give the monomer, 1-N-(5-ethenylpyridin-2-yl)-3-N-(pyridin-2-yl)benzene-1,3-dicarboxamide, as a yellow solid.

EXAMPLE 2

The monomer of formula II, where $R^1$, $R^2$, $R^3$, $R^4$ and $R^5$ are all hydrogen, was synthesised through the reaction of two equivalents of 2-amino-5-vinylpyridine with one equivalent of isophthaloyl dichloride in the presence of triethylamine.

Thus, isophthaloyl dichloride (102 mg, 0.5 mmol) was dissolved in anhydrous dichloromethane (20 mL) and placed under a dinitrogen atmosphere. The solution was then cooled to 0° C. using an ice bath. A solution of 2-amino-5-vinylpyridine (120 mg, 1 mmol) and triethylamine (101 mg, 1 mmol) in 10 mL dichloromethane was added dropwise to the cooled solution. On completion of the addition, the ice bath was removed and the solution allowed to stir at room temperature overnight. The reaction was then quenched by the addition of 10 mL water. The organic and aqueous layers were separated, then the organic layer was washed with saturated aqueous sodium hydrogen carbonate solution (2×10 mL) and water (10 mL), before being dried over magnesium sulfate. After filtration, the solvent was evaporated under reduced pressure. The residue was then purified by column chromatography, using silica gel as the stationary phase and ethyl acetate/hexanes as the mobile phase, to give the monomer, 1-N,3-N-bis(5-ethenylpyridin-2-yl)benzene-1,3-Dicarboxamide, as a yellow solid in 25% yield.

$^1$H NMR (CDCl$_3$, 400 mHz) δ: 8.33 (s, 2H), 8.12 (d, J=2.2 Hz, 2H), 7.97 (dd, 7.8, 2.3 Hz, 2H), 7.92 (s, 1H), 7.66 (dd), J=8.3, 2.3 Hz, 2H), 7.55 (t, J=7.7 Hz, 1H), 6.94 (d, J=8.3 Hz, 2H), 6.60 (dd, J=17.6, 11.1 Hz, 2H), 5.77 (d, J=17.6 Hz, 2H), 5.40 (d, J=11.0 Hz, 2H)

EXAMPLE 3

The monomer of Example 2 was studied for its ability to bind to a biotin derivative, the methyl ester of biotin, using a nuclear magnetic resonance titration method. The monomer of Example 2 bound the methyl ester of biotin with $K_a$=1220 M$^{-1}$ in deuterated chloroform. Such association constants are known to allow for the success of the stoichiometric imprinting protocols described further in this document.

EXAMPLE 4

This monomer of formula IV, where $R^1$, $R^2$, $R^3$, $R^4$ and $R^5$ are all hydrogen, was synthesised in two steps, as depicted below.

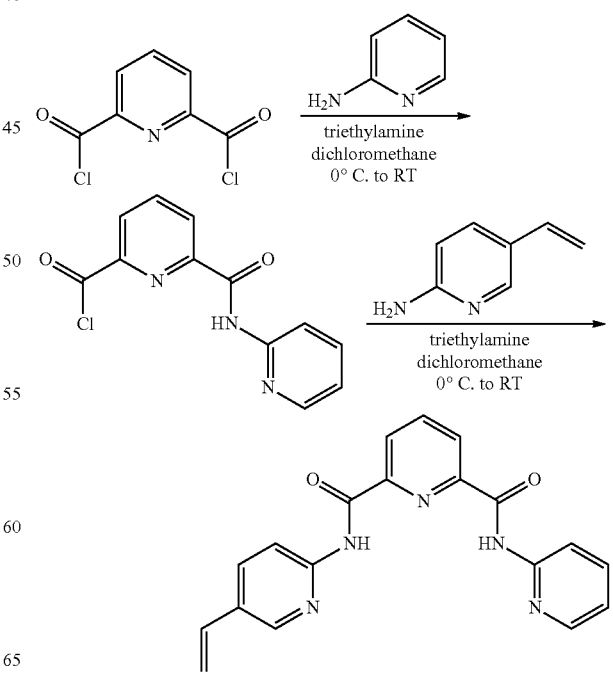

Pyridine-2,6-dicarbonyl dichloride (102 mg, 0.5 mmol) is dissolved in anhydrous dichloromethane (20 mL) and placed under a dinitrogen atmosphere. The solution is then cooled to 0° C. using an ice bath. A solution of 2-aminopyridine (94 mg, 0.5 mmol) and triethylamine (51 mg, 0.5 mmol) in 10 mL dichloromethane is added dropwise to the cooled acid chloride solution. On completion of the addition, the ice bath is removed and the solution is allowed to stir at room temperature for 3 hours. At this point, the solution is cooled again to 0° C. using an ice bath and a solution of 2-amino-5-vinylpyridine (60 mg, 0.5 mmol) and triethylamine (51 mg, 0.5 mmol) in 10 mL dichloromethane is added dropwise to the cooled solution. On completion of the addition, the ice bath is removed and the solution allowed to stir at room temperature overnight. The reaction is then quenched by the addition of 10 mL water. The organic and aqueous layers are separated, then the organic layer is washed with saturated aqueous sodium hydrogen carbonate solution (2×10 mL) and water (10 mL), before being dried over magnesium sulfate. After filtration, the solvent is evaporated under reduced pressure. The residue is then purified by column chromatography using silica gel as the stationary phase and ethyl acetate/hexanes as the mobile phase, to give the monomer, 2-N-(5-ethenylpyridin-2-yl)-6-N-(pyridin-2-yl)pyridine-2,6-dicarboxamide, as a yellow solid.

EXAMPLE 5

The monomer of formula V, where $R^1$, $R^2$, $R^3$, $R^4$ and $R^5$ are all hydrogen, was synthesised through the reaction of two equivalents of 2-amino-5-vinylpyridine with one equivalent of pyridine-2,6-dicarbonyl dichloride (Sigma Aldrich) in the presence of triethylamine, as described for the preparation of the compound of formula II in Example 2.

Thus, pyridine-2,6-dicarbonyl chloride (102 mg, 0.5 mmol) is dissolved in anhydrous dichloromethane (20 mL) and placed under a dinitrogen atmosphere. The solution is then cooled to 0° C. using an ice bath. A solution of 2-amino-5-vinylpyridine (120 mg, 1 mmol) and triethylamine (101 mg, 1 mmol) in 10 mL dichloromethane is added dropwise to the cooled solution. On completion of the addition, the ice bath is removed and the solution allowed to stir at room temperature overnight. The reaction is then quenched by the addition of 10 mL water. The organic and aqueous layers are separated, then the organic layer is washed with saturated aqueous sodium hydrogen carbonate solution (2×10 mL) and water (10 mL), before being dried over magnesium sulfate. After filtration, the solvent is evaporated under reduced pressure. The residue is then purified by column chromatography, using silica gel as the stationary phase and ethyl acetate/hexanes as the mobile phase, to give the monomer, 2-N,6-N-bis(5-ethenylpyridin-2-yl)pyridine-2,6-dicarboxamide, as a yellow solid.

EXAMPLE 6

The polymer is synthesised by free radical polymerisation of a mixture of any one of the monomers prepared as described in Examples 1-4 and at least one cross-linking monomer, which may be ethyleneglycol dimethacrylate, trimethyloylpropanetrimethacrylate, pentaerythritol triacrylate, a bis-acrylamide or divinylbenzene, in the presence of a solvent and a template and an initiator, which may be azobisisobutyronitrile. Further non-crosslinking monomers, that can be acrylamide, methacrylamide or 2-hydroxyethylmethacrylate, can also be added. The template can be biotin or a derivative thereof, such as an ester, amide, carbonate or carbamate. After polymerisation, the template is removed from the polymer by a washing procedure, which may be a continuous extraction with methanol.

Specifically, biotin methyl ester (258 mg, 1 mmol), the monomer of Example 2 (370 mg, 1 mmol) and ethyleneglycol dimethacrylate (3.96 g, 20 mmol) are dissolved in chloroform (5.6 mL) in a glass tube. Initiator (AIBN, 43.3 mg, 1% w/w total monomers) is added and the solution cooled on ice. Dinitrogen is sparged through the solution for ten minutes to remove dissolved oxygen and then the tube is sealed. The polymerisation is initiated by placing the sealed tube in a thermostat water bath set at 60° C.) and the polymerisation is allowed to continue at this temperature for 24 hours. After this time, the tube is removed from the water bath and smashed to extract the monolithic polymer. The polymer is roughly broken into smaller pieces and then subjected to continuous extraction with methanol in a Soxhlet apparatus for 24 hours, to remove template and unreacted monomers. The extracted polymer is then further crushed and sized to yield particles of the desired size range, e.g. 25-36 microns for chromatographic use or 36-63 microns for use in solid phase extraction.

EXAMPLE 7

The polymer prepared according to Example 6 is used for the selective separation of biotin, low molecular weight biotin derivatives and analogous compounds, and biotinylated biomacromolecules from complex mixtures. This can be done in chromatographic, batch or membrane modes.

For example, MIP particles (25-36 microns) are packed into a HPLC column, which is then attached to the HPLC, and used as the stationary phase in a liquid chromatographic separation. A sample containing a mixture, including a biotinylated species, is injected onto the column and flows through the column under the influence of the chosen mobile phase. The transport of the biotinylated species along the length of the column under the influence of the mobile phase is preferentially retarded relative to non-biotinylated species due to specific interactions between the MIP stationary phase and the biotinylated species. Thus, the biotinylated species elutes from the column later and is effectively separated from other species present in the mixture.

The invention claimed is:

1. A polymerisable monomer comprising a recognition cleft for biotin, a biotin derivative, a biotin analogue or a biotinylated molecule, the monomer comprising i) an isophthalic acid derivative or a pyridine-2,6-dicarboxylic acid derivative and ii) a vinyl-2-aminopyridine derivative for use as part of a molecularly imprinted polymer.

2. A polymerisable monomer according to claim 1, wherein the monomer is prepared from i) an isophthalic acid derivative or a pyridine-2,6-dicarboxylic acid derivative, ii) a vinyl-2-aminopyridine derivative and optionally iii) a 2-aminopyridine, to define a recognition cleft for biotin, a biotin derivative, a biotin analogue or a biotinylated molecule.

3. A polymerisable monomer according to claim 1, wherein the ratio of the isophthalic acid derivative or pyridine-2,6-dicarboxylic acid derivative to the vinyl-2-aminopyridine derivative is 1:2.

4. A polymerisable monomer according to claim 1, wherein the ratio of the isophthalic acid derivative or pyridine-2,6-dicarboxylic acid derivative to the vinyl-2-aminopyridine derivative is 1:1 and the monomer further includes 2-aminopyridine residue.

5. A polymerisable monomer according to claim 1, wherein the monomer is a compound of
Formula (I):

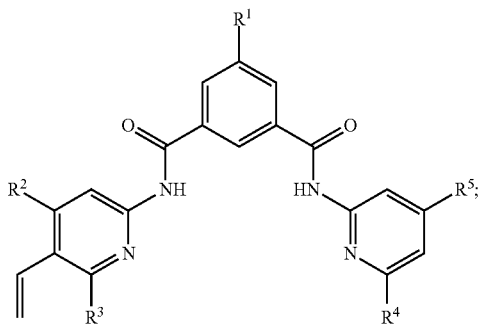

Formula (II):

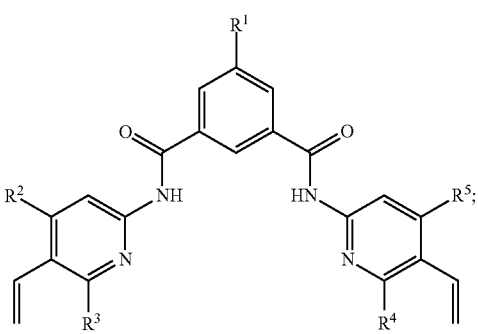

Formula (IV):

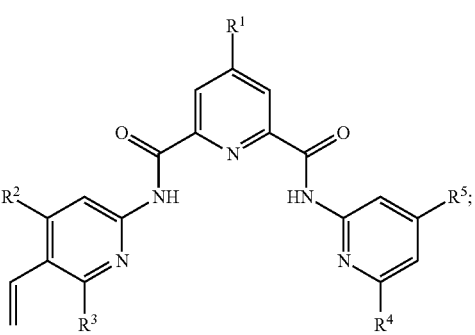

or
Formula (V):

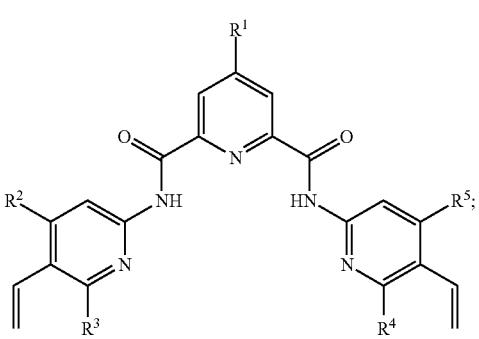

wherein each of $R^1$, $R^2$, $R^3$, $R^4$ and $R^5$ is independently selected from H, an alkyl group comprising 1-10 carbon atoms, an alkoxy group comprising 1-10 carbon atoms, an aryl group with up to five substituents, an amino group, an amido group, and a halogen.

6. A polymerisable monomer according to claim 5, wherein the monomer is of Formula (I) or Formula (II) and $R^1$ is a tert-butyl group.

7. A polymerisable monomer according to claim 5, wherein each of $R^2$, $R^3$, $R^4$ and $R^5$ is independently selected from H or a methyl group.

8. A polymerisable monomer according to claim 1, wherein the isophthalic acid derivative is a 2,6-pyridine dicarboxylic acid derivative.

9. A polymerisable monomer according to claim 5, wherein the monomer is a compound of Formula (IV) or Formula (V), and $R^1$ is a methoxy, ethoxy, propoxy, 3-methylbutoxy, dimethylamino, diethylamino, dipropylamino, piperidino or morpholino group.

10. A polymerisable monomer according to claim 1, wherein the vinyl-2-aminopyridine derivative is 2-amino-5-vinylpyridine.

11. A polymerisable monomer according to claim 1, wherein the biotin derivative is a salt.

12. A polymerisable monomer according to claim 11, wherein the biotin derivative is an ester, amide, carbonate or carbamate.

13. A molecularly imprinted polymer comprising:
  i) at least one monomer comprising
    (a) an isophthalic acid derivative or a pyridine-2,6-dicarboxylic acid derivative and;
    (b) a vinyl-2-aminopyridine derivative; and
  ii) at least one cross-linking monomer;
  wherein the polymer is prepared in the presence of a template molecule is selected from the group consisting of biotin, a biotin derivative, a biotin analogue and a biotinylated molecule.

14. A molecularly imprinted polymer according to claim 13, wherein the biotin derivative is a salt.

15. A molecularly imprinted polymer according to claim 13, wherein the biotin derivative is an ester, amide, carbonate or carbamate.

16. A method for preparing a monomer, wherein the method comprises reacting two equivalents of a vinyl-2-aminopyridine derivative with one equivalent of an isophthalic acid derivative to form the monomer, wherein the monomer comprises a recognition cleft for biotin, a biotin derivative, a biotin analogue or a biotinylated molecule.

17. A method according to claim 16, wherein the method comprises:
  a) dissolving a diacid derivative in a solution using an anhydrous solvent;
  b) cooling the mixture to 0° C.;
  c) adding a solution of vinyl-2-aminopyridine derivative and a tertiary amine;
  d) warming the mixture to room temperature and stirring for 24 hours; and
  e) quenching the reaction by addition of water, separating the resulting organic and aqueous phases, washing and drying the organic phase, before evaporating the solvent to leave a solid monomer.

18. A method according to claim 17, wherein the ratio of the diacid derivative to the vinyl-2-aminopyridine derivative is 1:2.

19. A method according to claim 17, wherein the ratio of the diacid derivative to the vinyl-2-aminopyridine derivative is 1:1 and the method further comprises adding one equivalent of 2-aminopyridine before addition of one equivalent of a vinyl-2-aminopyridine derivative.

20. A molecularly imprinted polymer according to claim 13, wherein the cross-linking monomer is at least partially hydrophobic.

21. A molecularly imprinted polymer according to claim 20, wherein the cross-linking monomer is a di-, tri- or tetra-vinyl monomer selected from the group comprising: ethyleneglycol dimethacrylate, divinyl benzene and trimethyloylpropane trimethacrylate, bisacrylamides and pentaerythritol triacrylate.

22. A molecularly imprinted polymer according to claim 13, wherein the cross-linking monomer is at least partially hydrophilic.

23. A molecularly imprinted polymer according to claim 22, wherein the cross-linking monomer is selected from the group comprising: pentaerythritol triacrylate and bisacrylamides.

24. A method according to claim 16, comprising free-radical polymerisation of at least two of the monomers with at least one cross-linking monomer in the presence of a template molecule, wherein the template molecule is selected from the group consisting of biotin, a biotin derivative and a biotinylated molecule.

25. A method according to claim 24, wherein the method comprises:
    i) formation of a template-monomer complex in a solvent and a polymerisation initiator, using non-covalent binding;
    ii) polymerisation with an excess of a cross-linking reagent initiated by a suitable polymerisation initiator; and
    iii) removal of the template to yield a complementary binding site for the template,
    wherein the template is selected from the group consisting of biotin, a biotin derivative and a biotinylated molecule.

26. A method according to claim 24, wherein the biotin derivative is a salt selected from the group comprising: an ester, an amide, a carbonate and a carbamate.

27. A method according to claim 24, wherein the template-monomer complex is dissolved in a solvent selected from the group comprising: chloroform, toluene, acetonitrile, tetrahydrofuran or dimethylformamide.

28. A method according to claim 25, wherein the polymerisation initiator is an azobisisobutyronitrile.

29. A method according to claim 24, wherein, after polymerisation, the template is removed from the polymer by a washing procedure.

* * * * *